(12) United States Patent
Oh (10) Patent No.: US 11,318,026 B2
(45) Date of Patent: May 3, 2022

(54) IMPLANT HAVING ENHANCED INITIAL FIXATION FORCE

(71) Applicant: Synaptic Innovations, LLC, Dallas, TX (US)

(72) Inventor: Michael C. Oh, Dallas, TX (US)

(73) Assignee: SYNAPTIC INNOVATIONS, LLC, Dallas, TX (US)

(*) Notice: Subject to any disclaimer, the term of this patent is extended or adjusted under 35 U.S.C. 154(b) by 0 days.

(21) Appl. No.: 16/937,887

(22) Filed: Jul. 24, 2020

(65) Prior Publication Data

US 2022/0023067 A1   Jan. 27, 2022

(51) Int. Cl.
  *A61F 2/46* (2006.01)
  *A61F 2/30* (2006.01)

(52) U.S. Cl.
  CPC ........ *A61F 2/4601* (2013.01); *A61F 2/30749* (2013.01); *A61F 2/4611* (2013.01); *A61F 2002/30622* (2013.01); *A61F 2002/4615* (2013.01); *A61F 2002/4625* (2013.01); *A61F 2002/4627* (2013.01); *A61F 2002/4687* (2013.01)

(58) Field of Classification Search
  CPC ............ A61B 17/7097; A61B 17/8802; A61B 17/8805; A61B 17/8822; A61B 17/8833; A61B 17/8841; A61F 2/4601; A61F 2/4611; A61F 2002/444; A61F 2002/447; A61F 2002/4455; A61F 2002/4631
  See application file for complete search history.

(56) References Cited

U.S. PATENT DOCUMENTS

| | | | | |
|---|---|---|---|---|
| 7,717,947 B1 * | 5/2010 | Wilberg | ............... | A61B 17/864 606/304 |
| 8,556,949 B2 * | 10/2013 | Teisen | ................... | A61F 2/4455 606/327 |
| 9,055,980 B2 * | 6/2015 | Biedermann | ...... | A61B 17/7035 |
| 9,936,992 B2 | 4/2018 | Russell et al. | | |
| 2005/0107800 A1 * | 5/2005 | Frankel | ............. | A61B 17/1655 606/92 |
| 2006/0004455 A1 * | 1/2006 | Leonard | ................ | A61F 2/4425 623/17.15 |
| 2007/0093899 A1 * | 4/2007 | Dutoit | ................ | A61B 17/8858 623/17.11 |
| 2009/0187249 A1 * | 7/2009 | Osman | .................... | A61L 27/54 623/17.16 |
| 2011/0046739 A1 * | 2/2011 | Oglaza | .................. | A61F 2/4601 623/17.15 |

* cited by examiner

*Primary Examiner* — Anu Ramana
(74) *Attorney, Agent, or Firm* — WHDA, LLP

(57) ABSTRACT

The present invention provides an implant having an enhanced initial fixation force, and more particularly, to an implant that may maintain a fixed state without relative movement with respect to vertebral bodies until fusion is completely performed. The implant includes: an implant body inserted between vertebral bodies; and an injection unit installed in the implant body, and configured to inject bone cement into the vertebral bodies.

6 Claims, 10 Drawing Sheets

IMPLANT HAVING ENHANCED INITIAL FIXATION FORCE

BACKGROUND OF THE INVENTION

1. Field of the Invention

The present invention relates to an implant having an enhanced initial fixation force, and more particularly, to an implant that may maintain a fixed state without relative movement with respect to vertebral bodies until fusion is completely performed.

2. Description of the Related Art

A vertebral body includes 32 to 35 vertebrae forming a body, and intervertebral discs, i.e., spinal discs arranged between the vertebrae, and is a portion forming a backbone of a human body that connects an upper skull and a lower pelvis.

The vertebrae include 7 cervical vertebrae, 12 thoracic vertebrae, 5 lumbar vertebrae, 5 sacra, and 3 to 5 coccyges from the top. In the case of an adult, 5 sacra are fused together to form one sacral vertebra, and 3 to 5 coccyges are fused together to form one tailbone.

As one of the treatment methods for treating serious spinal diseases for a long time, there is spinal fusion. Such spinal fusion is a surgical method, which includes removing an intervertebral disc, and inserting a cage that replaces the intervertebral disc to fuse adjacent vertebral bodies to each other.

When performing the spinal fusion in the lumbar vertebrae, it may be divided into several techniques: posterior lumbar interbody fusion (PLIF), transforaminal lumbar interbody fusion (TLIF), direct lateral lumbar interbody fusion (DLIF), oblique lumbar interbody fusion (OLIF), and anterior lumbar interbody fusion (ALIF) depending on an insertion direction of the cage.

The PLIF is a method, which includes incising a back along a centerline of the spine, opening so as to expose all of the vertebral bodies, removing a portion of the posterior side of the vertebra, then removing the disc, and inserting a PLIF cage between the vertebrae.

The PLIF has been performed from the oldest among the spinal fusions, and is an absolutely necessary method when fusing two or three joints. However, due to a surgical process, the PLIF has various disadvantages such as high possibility of adhesion to nerves, ligaments and muscles, extended period of time for healing due to a large incision area, and serious aftereffects for some people.

The PLIF cage is the smallest of the cages used in all spinal fusions, wherein a pair of small cages are displaced on left and right sides of the spine.

The TLIF is a surgical method, which includes incising the back in a small area along both sides of a spinal muscle, exposing the vertebral bodies to a minimum, and then inserting the TLIF cage by replacing the disc while removing a spinal joint site in a direction coming out of a neuropore. This surgical technique is suitable for a case of one joint due to advantages of less bleeding, and reduced operation time. However, if an operation over multiple sites is required, the PLIF surgery should be performed. Most of the TLIF cage is formed in an arch shape, such that it is placed in the vertebral bodies and rotated so that a convex portion of the TLIF cage faces a stomach. The TLIF cage is larger than the PLIF cage, but its support area is smaller than a DLIF cage or ALIF cage which will be described below.

The ALIF has various advantages, such as fast recovery from the operation and no need to worry about adhesions. However, the ALIF has a disadvantage of requiring highly advanced surgical skill because the operation is performed by incising an anterior (stomach) to bypass intestines, and approaching the spine. The ALIF cage has an advantage of having the largest support area among all spinal fusion cages.

The DLIF was developed to overcome the disadvantages of the ALIF, PLIF, and TLIF. Since the operation is performed through flank incision, the DLIF has advantages that an interval of stenosed sites between the vertebrae may be more greatly widened than the conventional surgeries performed by incision of the back, and there is almost no damage to surrounding tissues. However, since a psoas muscle and peritoneum are arranged around a route to be operated, there is a problem of causing thigh muscle paralysis if there is a surgical mistake during the operation. The DLIF cage is smaller than the ALIF cage, but larger than the PLIF cage or TLIF cage.

Compared to the DLIF, the safer and more effective method is the OLIF. The OLIF has advantages that the operation route is formed in a direction inclined from the flank, and the operation is possible between the 4th lumbar vertebra (L4) and the 5th lumbar vertebra (L5), which are difficult to operate by the DLIF due to the psoas muscle and peritoneum. In addition, the possibility of damaging the nerves, which may be a problem in the DLIF, is significantly less.

In such spinal fusion, the bones may be stably formed only when there is no relative movement between the cage and the vertebrae during the bones growing in or around the cage such that the vertebrae adjacent to upper and lower sides of the cage are fused to each other. If there is a relative movement between the cage and the vertebrae, the bone is not formed, or the upper and lower bones grow, but they are adhered to each other so as not to be fused.

To solve these problems, the relative movement between the cage and the vertebrae is suppressed by installing additional plates, or installing separate screws on adjacent vertebrae, respectively, and fixing rods to a coupler of both screws.

However, this method not only requires a separate implant, but also has a problem of lengthening the operation time due to additional surgery.

PRIOR ART DOCUMENT

Patent Document (Patent Document 1) U.S. Pat. No. 9,936,992

SUMMARY OF THE INVENTION

In consideration of the above-mentioned circumstances, it is an object of the present invention to provide an implant that may maintain a fixed state without a relative movement with respect to vertebral bodies until fusion is completely performed.

To achieve the above object, according to an aspect of the present invention, there is provided an implant including: an implant body inserted between vertebral bodies; and an injection unit installed in the implant body, and configured to inject bone cement into the vertebral bodies.

The injection unit may include a digger configured to dig into an end plate through rotation.

The digger may be connected to an injection tube having an injection port, and the digger may have an outlet port configured to discharge the bone cement introduced through the injection port.

The digger may include digger blades formed at both ends thereof to dig into the end plate.

An injection fastening part may be formed around the injection port, and an operation device may be connected to the injection fastening part to rotate the digger.

The injection fastening parts may be radially disposed around the injection port.

The injection fastening parts may be a plurality of protrusions or grooves longitudinally formed on an outer circumferential surface of an end of the injection tube around the injection port.

The injection unit may include a keel part configured to dig into the end plate in a direction, in which the implant body is inserted.

The implant body may include guide parts formed therein to guide the keel part, and the keel part may include sliders formed on both sides thereof, on which the guide parts move.

The keel part may include a plurality of outlet ports formed therein along a longitudinal direction thereof, and the outlet ports have a cross-sectional area decreasing toward a distal part.

The implant body may include a guide block formed on one side thereof to guide the keel part to be introduced.

The injection unit may include an anchor configured to penetrate the end plate in an inclined direction.

The injection unit may include a lifter configured to penetrate the end plate in a vertical direction of the implant body.

A height of the lifter may be increased by an expansion device inserted through an operation hole formed in the implant body, and the lifter may include an upper part and a lower part, and the upper part and the lower part may include position retaining protrusions formed thereon which are engaged with each other to maintain an increased height thereof.

The injection unit may include a bone screw mounted on a plate attached to the implant.

The bone screw may include an injection port formed in a head thereof and outlet ports formed in a threaded part thereof to be communicated with the injection port.

The plate may be fixed to the implant by a plate fixing screw.

The implant may include bone screw seats formed therein to allow the bone screw to be introduced.

According to the present invention, it is possible to provide an implant capable of maintaining a fixed state without a relative movement with respect to vertebral bodies until fusion is completely performed. In particular, since the bone cement may cause serious problems such as vascular occlusion when it leaks into the body, the implant of the present invention has a structure that may accurately inject the bone cement only into the vertebral body.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, preferable embodiments of the present invention will be described with reference to the accompanying drawings. Referring to the drawings, wherein like reference characters designate like or corresponding parts throughout the several views. In the embodiments of the present invention, a detailed description of publicly known functions and configurations that are judged to be able to make the purport of the present invention unnecessarily obscure will not be described.

Figure 2:
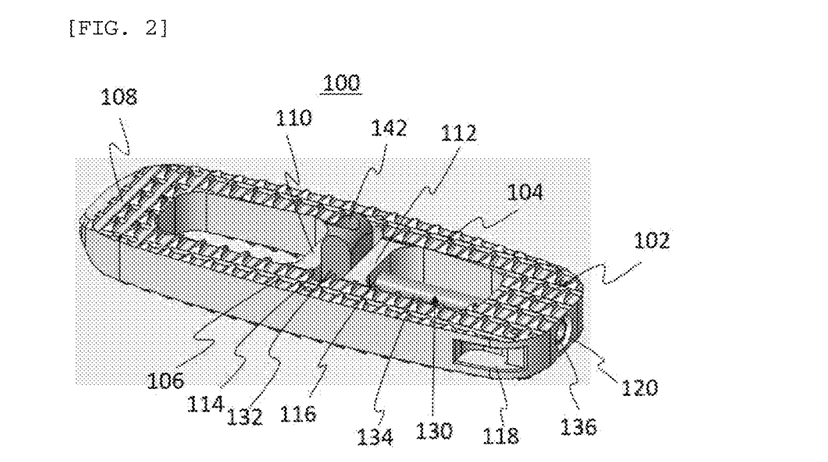
FIG. 2 is a perspective view illustrating a state, in which a digger of an injection unit in the implant of Embodiment 1 may rotate to inject bone cement into the vertebral body.
Figure 3:
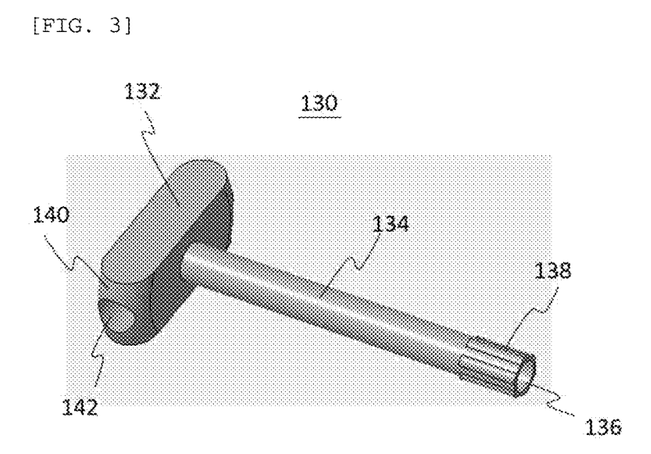
FIG. 3 is a perspective view illustrating the injection unit of the implant of Embodiment 1.

First, an implant 100 according to Embodiment 1 of the present invention will be described with reference to FIGS. 1 to 3.

The implant 100 basically includes an implant body inserted between vertebral bodies, and an injection unit 130, which is installed in the implant body and may serve to inject bone cement into the vertebral body through an end plate.

The implant body may be made of a polymer material such as polyether ether ketone (PEEK), which is harmless to a human body, or may be made of a mixture obtained by combining segments of the polymer material and segments of a metal material with each other. At this time, the metal material uses metal such as titanium, stainless steel, or the like, which is harmless to the human body. Of course, the entire body may also be made of a metal material.

Figure 1:
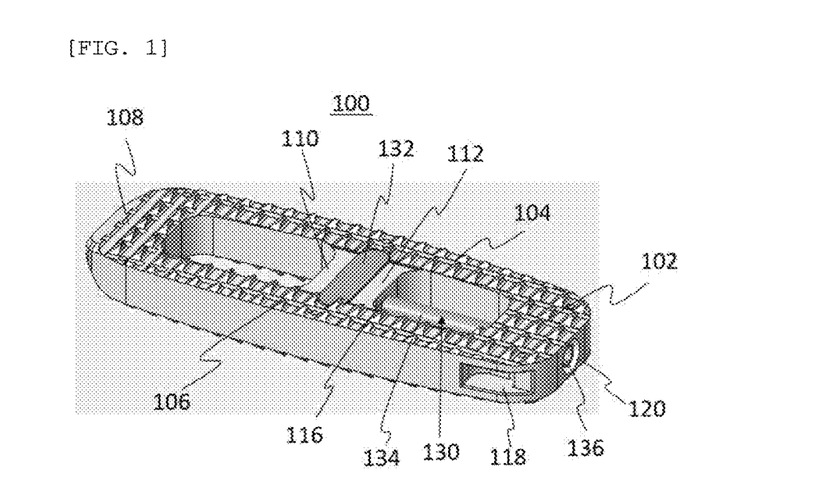
FIG. 1 is a perspective view illustrating an implant according to Embodiment 1 of the present invention in a state of inserting into a vertebral body.

As illustrated in FIG. 1, the implant body includes a distal part 108, which is a region where an insertion thereof into the vertebral body side is started, a proximal part 102 disposed on a side opposite to the distal part 108, and side parts 104 and 106 formed between the proximal part 102 and the distal part 108. The implant body is formed in a substantially rectangular shape defined by the proximal part 102, the side parts 104 and 106, and the distal part 108, but it is not limited thereto, and may include various variants.

A window into which a bone material is inserted may be formed in a region surrounded by the proximal part 102, the side parts 104 and 106, and the distal part 108. As the bone graft, known materials such as autologous bone or BMP may be used.

The proximal part 102 may include holder seats 118 formed at sides thereof to be connected with a device for inserting the implant 100. The holder seat 118 may be formed in various shapes such as a groove, a screw hole and the like. In addition, bridges 110 and 112 may be formed between the pair of side parts 104 and 106 for reinforcing the implant. In particular, in Embodiment 1, a pair of bridges 110 and 112 may be arranged for installation of the injection unit 130, and a digger receiving cavity 114, in which a digger 132 of the injection unit 130 can be located, may be disposed therebetween.

The injection unit 130 is installed in the digger receiving cavity 114 of the implant body. The injection unit 130 of Embodiment 1 is characterized by having the digger 132. As illustrated in FIG. 3, the injection unit 130 includes a digger 132, which has a height equal to or lower than that of the implant 100, and an injection tube 134 integrally connected with the digger 132.

The injection tube 134 is rotatably supported by an operation hole 120 formed in the proximal part 102 and a through hole 116 formed in the bridge 112.

The injection tube 134 is provided with an injection port 136 formed at one end thereof to allow a bone material to be injected from an outside, and an outlet port 142 formed at the other end thereof to be communicated with the injection port 136 formed in the digger 132. In addition, the injection tube 134 has an injection fastening part 138 formed at an end thereof, that is, a portion located in the operation hole 120. The injection fastening part 138 may be fastened with an operation device (not illustrated) to receive a rotational driving force of the operation device to rotate the digger 132.

The injection fastening parts 138 may be radially disposed around the injection port 136. In Embodiment 1, the injection fastening part may include a plurality of protrusions formed on an outer circumferential surface of an end of the injection tube 134 to be radially disposed along the circumference. In this case, a plurality of grooves may be formed other than the plurality of protrusions. Accordingly, the operation device (not illustrated) may be fastened with the injection fastening part 138 in a longitudinal direction of the injection tube 134. Likewise, when moving the operation device in a direction opposite to the direction, in which the injection fastening part 138 is coupled, the operation device may be easily separated from the injection fastening part 138.

The digger 132 is rotated by the rotation of the injection tube 134, and is inserted into the vertebral body by passing through the end plate. At this time, outlet port 142 is opened into the vertebral body. Therefore, when injecting the bone cement from the injection port 136, the bone cement, which is injected through the injection port 136 and discharged from the outlet port 142, is filled in the vertebral body, and consequently, the vertebral body is hardened. As a result, the digger 132 may be fixed to the vertebral body.

Consequently, it is possible to immediately expect an initial fixing force by the bone cement in an initial state, in which the implant 100 is inserted into the vertebral body. Therefore, the implant 100 may be seated without a relative movement with respect to the vertebral body, such that bones are formed in and out of the implant 100, and thereby adjacent vertebral bodies may be stably fused.

Figure 4:
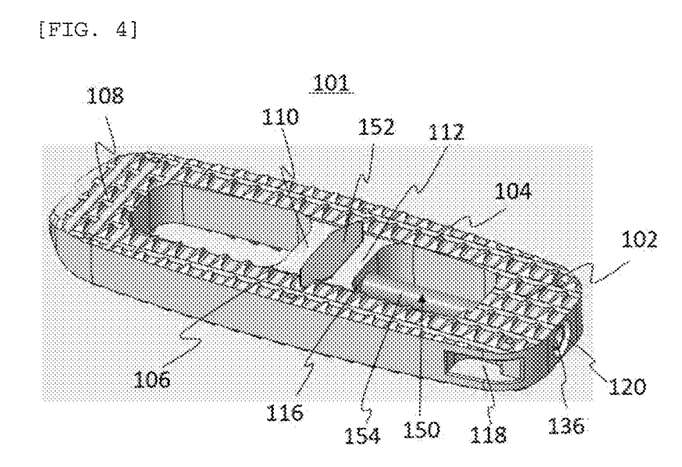
FIGS. 4 to 6 are perspective views illustrating a variant of Embodiment 1.
Figure 5:
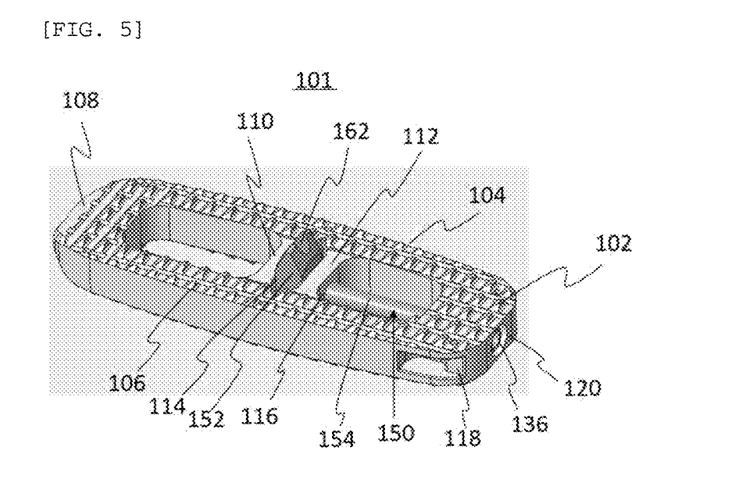
Figure 6:
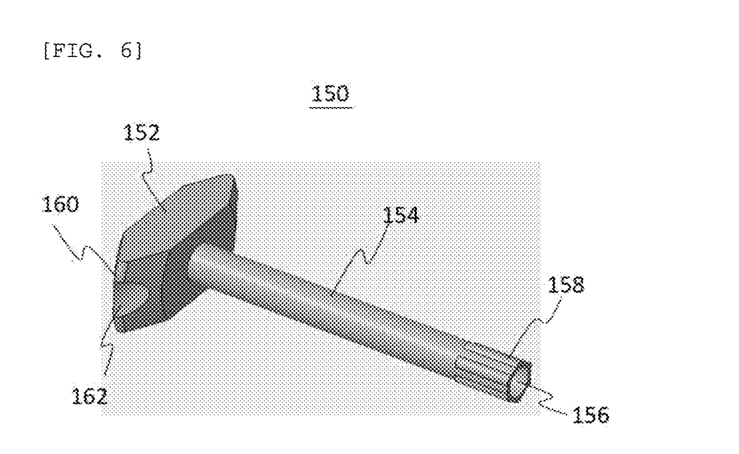

FIGS. 4 to 6 illustrates an implant 101 according to a variant of Embodiment 1. The same parts as those of Embodiment 1 will be denoted by the same reference numerals and will not be described in detail.

The implant 101 according to the variant is different from the implant 100 according to Embodiment 1 in the shape of an injection unit 150. That is, there is no difference in the injection tube 154, the injection fastening part 158, and the injection port 156 therebetween, but the digger 152 is different in shape.

The injection unit 130 of Embodiment 1 has a characteristic that the digger 132 has digger blades 140 formed at both ends thereof in a substantially round shape with a height increasing toward the outlet port 142. On the other hand, the injection unit 150 of the variant has a characteristic that the digger 152 has digger blades 160 formed at both ends thereof in a sharp shape with a height increasing toward the outlet port 162. As a result, the digger 132 of Embodiment 1 may be suitable for patients with a slightly weaker vertebral body due to osteoporosis and the like, and the digger 152 of the variant may be suitable for patients with hard bone tissues such as young or male patients.

Next, an implant 200 of Embodiment 2 will be described with reference to FIGS. 7 to 11.

The implant 200 includes an implant body and injection units 230 and 250 similar to Embodiment 1. The implant body also includes a proximal part 202, side parts 204 and 206, and a distal part 208, and has holder seats 218 to be coupled with the device for inserting the implant.

Figure 7:
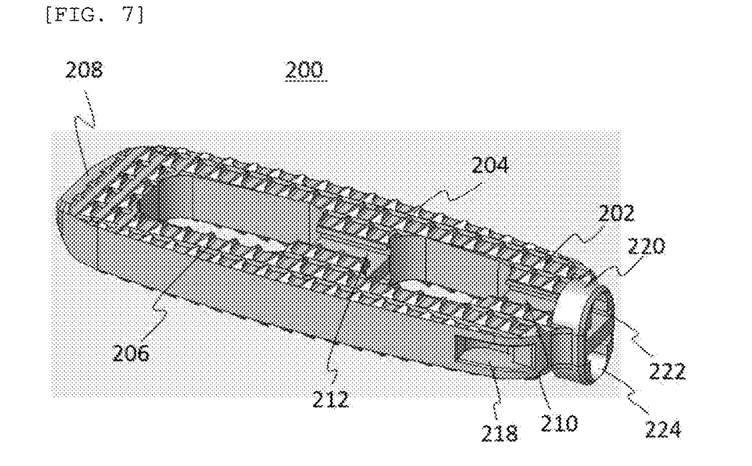
FIG. 7 is a perspective view illustrating an implant according to Embodiment 2 of the present invention in a state of inserting into a vertebral body.
Figure 8:
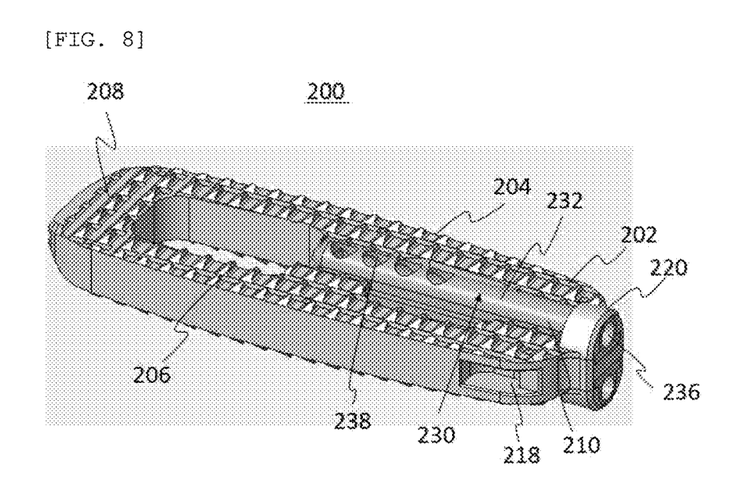
FIG. 8 is a perspective view illustrating a state, in which a keel part of an injection unit is inserted in the implant of Embodiment 2.

The implant body includes guide parts 210 and 212 formed therein. The injection units 230 and 250 are inserted into the guide parts 210 and 212. The guide parts 210 and 212 may be formed in a substantially rail shape, and as long as they can stably guide the injection units 230 and 250, there is no limitation in the shape.

Figure 9:
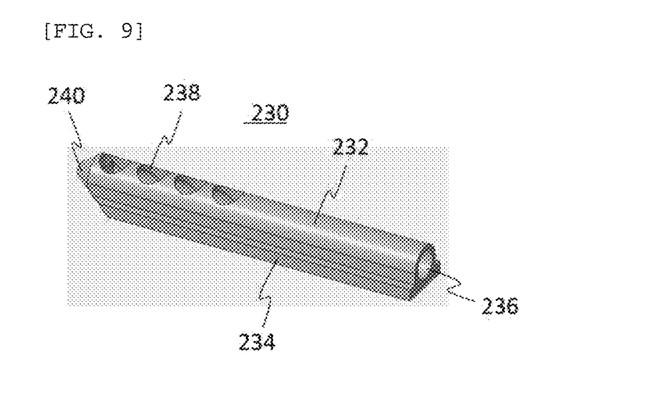
FIG. 9 is a perspective view illustrating the injection unit of the implant of Embodiment 2.
Figure 11:
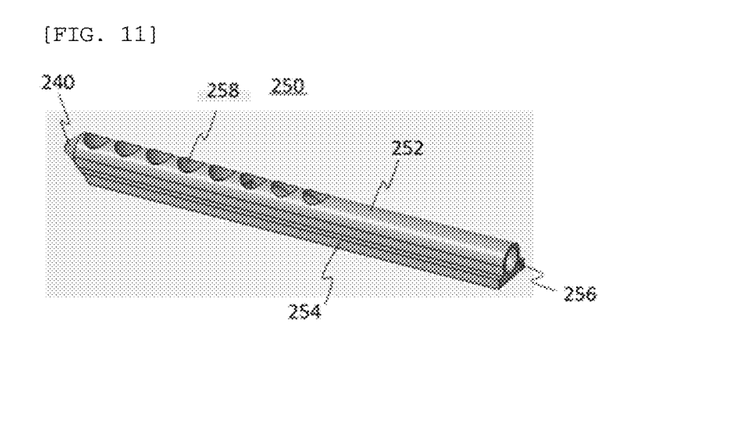

The injection units 230 and 250 include keel parts 232 and 252, respectively. That is, the keel parts 232 and 252 are characterized by digging into the end plate in a direction, in which the implant body is inserted. The keel parts 232 and 252 are provided with sliders 234 and 254 formed on both sides thereof, on which the guide parts 210 and 212 may slide.

Each of the keel parts 232 and 252 is provided with a sharp tip portion 240 formed at one end thereof to facilitate digging into the vertebral body.

In addition, the keel parts 232 and 252 may include a plurality of outlet ports 238 and 258 formed therein at an interval along the longitudinal direction thereof. At this time, it is preferable that the outlet ports 238 and 258 have a cross-sectional area decreasing toward the distal part so that the bone material may be constantly flown out. The outlet ports 238 and 258 should be arranged in a direction toward the inside of the vertebral body.

Figure 10:
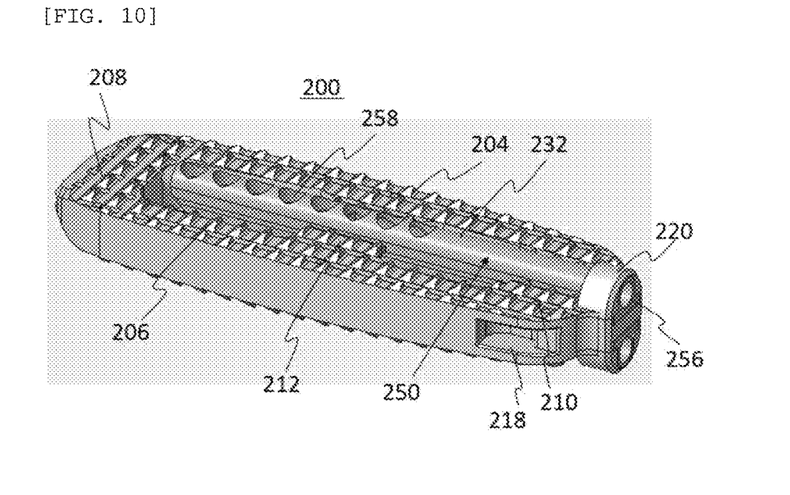
FIGS. 10 and 11 are perspective views illustrating a variant of Embodiment 2.

As illustrated in FIGS. 9 and 11, the keel parts 232 and 252 may include different lengths from each other as necessary. However, for stable coupling, as illustrated in FIG. 8, it is preferable that the length of the keel parts 232 and 252 is greater than 50% of the length of the implant body, or as illustrated in FIG. 10, less than 100% thereof. In addition, in order to guide the insertion of the keel parts 232 and 252, a guide block 220 may be further provided in the implant body. As illustrated in FIG. 7, the guide block 220 is formed in an approximately elliptical shape, and has guide ports 222 and 224 formed therein with being vertically arranged so that the keel parts 232 and 252 may be guided through the guide ports 222 and 224.

Next, an implant 300 of Embodiment 3 will be described with reference to FIGS. 12 to 14.

The implant 300 includes an implant body and an injection unit 330 similar to Embodiment 1. The implant body also includes a proximal part 302, side parts 304 and 306, and a distal part 308, and has holder seats 318 to be coupled with the device for inserting the implant. In addition, a bridge 310 is disposed between the side parts 304 and 306 in a lateral direction.

The injection unit 330 of the implant 300 is characterized by including an anchor 332 penetrating the end plate in an inclined direction.

Figure 13:
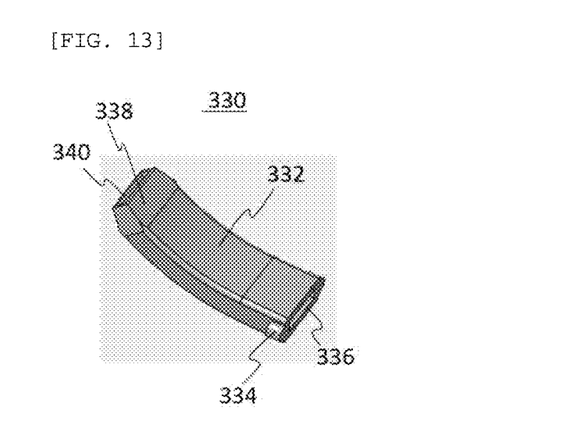
FIG. 13 is a perspective view of an injection unit used in Embodiment 3.
Figure 14:
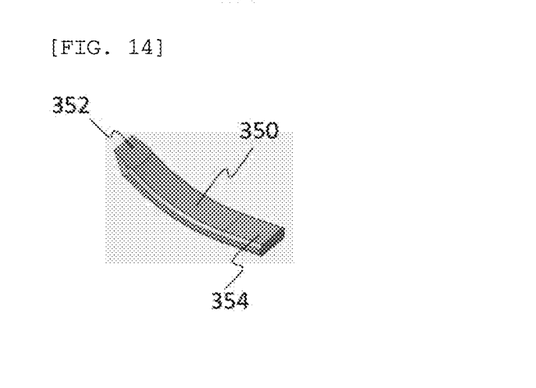
FIG. 14 is a perspective view of a perforation device used in Embodiment 3.

The anchor 332 has an injection port 336 and an outlet port 340 formed at both ends thereof, and as illustrated in FIG. 13, is bent upward or downward as a whole, wherein an anchor tip 338 is formed at one end thereof so as to have a cross-sectional area gradually decreasing toward the tip to facilitate the penetration into the end plate. In addition, the anchor 332 may have stoppers 334 disposed on the proximal part side to limit an insertion length of the anchor 332.

In addition, if directly inserting the anchor 332, not only the insertion itself is difficult but also bone tissue inflows into the outlet port 340 to prevent the discharge of the bone cement. Therefore, in order to solve this problem, a perforation device 350 as illustrated in FIG. 14 may be used. The perforation device 350 has a shape approximately similar to the anchor 332, but is formed as a solid body with a smaller cross-sectional area. Further, the perforation device 350 has a perforation device tip 352 sharply formed at one end thereof to facilitate the penetration into the end plate, and a perforation device gripping part 354 formed at the other end on the side opposite to the perforation device tip 352, which is a seat part that can be grasped by a device for holding the perforation device 350.

Figure 12:
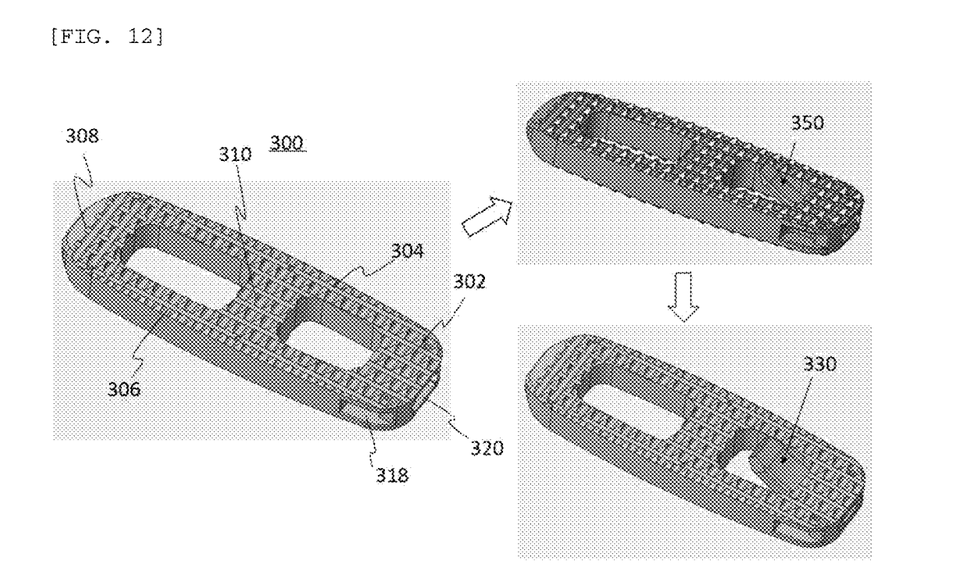
FIG. 12 is a perspective view illustrating an implant according to Embodiment 3 of the present invention.

Thus, as illustrated in FIG. 12, during an operation, the implant 300 is inserted into the vertebral bodies, the perforation device 350 is inserted into the implant through an operation hole 320 formed in the implant body to perforate into the end plate, the perforation device 350 is removed, and then the injection unit 330 is inserted into the implant body. Thereafter, the main cement is injected through the injection port 336 of the injection unit 330 so that the injection unit 330 can be fixed inside the vertebral body.

Figure 15:
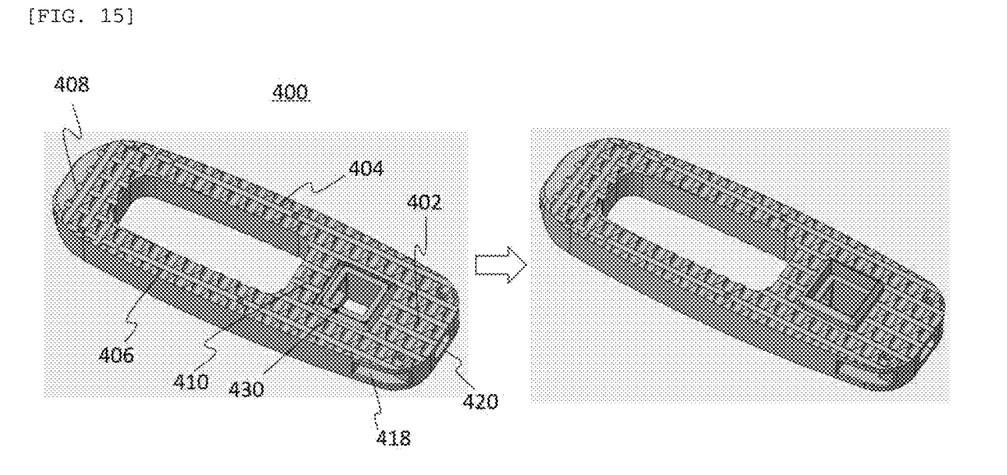
FIG. 15 is a perspective view illustrating an implant according to Embodiment 4 of the present invention.
Figure 16:
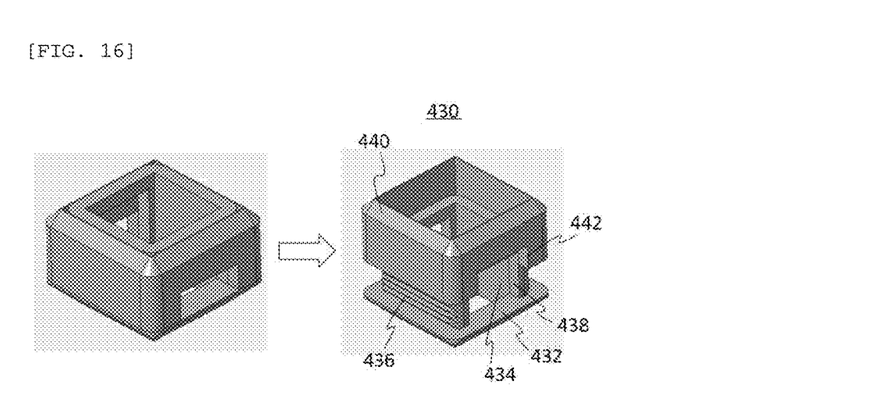
FIG. 16 is a perspective view of an injection unit of Embodiment 4.

Then, an implant 400 of Embodiment 4 will be described with reference to FIGS. 15 and 16. The implant 400 includes an implant body and an injection unit 430 similar to Embodiment 1. The implant body also includes a proximal part 402, side parts 404 and 406, and a distal part 408, and has holder seats 418 to be coupled with the device for inserting the implant. In addition, a bridge 410 is disposed between the side parts 404 and 406 in a lateral direction.

The injection unit 430 may include a lifter penetrating the end plate in a vertical direction of the implant body. The lifter has an upper part 440 and a lower part 434, wherein one of the upper part 440 and the lower part 434 may be inserted into the other one so as to move relative to each other. In Embodiment 4, the lower part 434 is configured to be inserted into the upper part 440.

In addition, the lower part 434 and the upper part 440 have a plurality of position retaining protrusions 436 formed on opposite outer sides thereof in a lateral direction along the vertical direction of the implant, respectively. When the lower part 434 and the upper part 440 are coupled with each other, it is possible to maintain a position of these parts by the position retaining protrusions 436 engaged with each other.

Further, the lower part 434 includes lower openings 438 formed in opposite sides thereof in a longitudinal direction thereof, and the upper part 440 includes upper openings 442 formed in opposite sides thereof at positions corresponding to the lower openings 438. When assembling, the lower openings 438 and the upper openings 442 may together form through holes into which an expansion device (not illustrated) is inserted. In addition, the lower part 434 may include a flange 432 formed at a bottom thereof so as to have the lowest height.

During an operation, the implant 400 is first inserted into the vertebral body, the expansion device (not illustrated) is inserted into an operation hole 420 formed in the implant body, and then the expansion device is operated to push up the lifter with being supported by the lower openings 438 and the upper openings 442. At this time, it is preferable that the expansion device is inserted through the openings formed in the lower part 434 and the upper part 440 in the longitudinal direction to break the end plate, as well as moves the lower part 434 and the upper part 440 in a direction away from each other. When the lifter extends by a predetermined height, the lower part 434 and the upper part 440 are maintained in the extended state by the position retaining protrusions 436, and the bone cement is injected into the injection unit 430 through the expansion device or other injection devices. Accordingly, the bone cement is injected into the vertebral body through the openings formed in the lower part 434 and the upper part 440 in the longitudinal direction, thereby securely fixing the injection unit 430 to the vertebral body.

Figure 17:
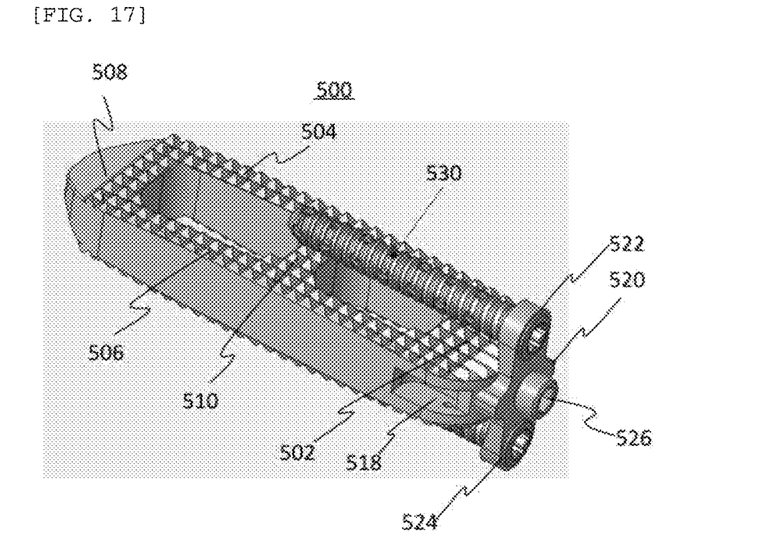
FIG. 17 is a perspective view illustrating an implant according to Embodiment 5 of the present invention.
Figure 18:
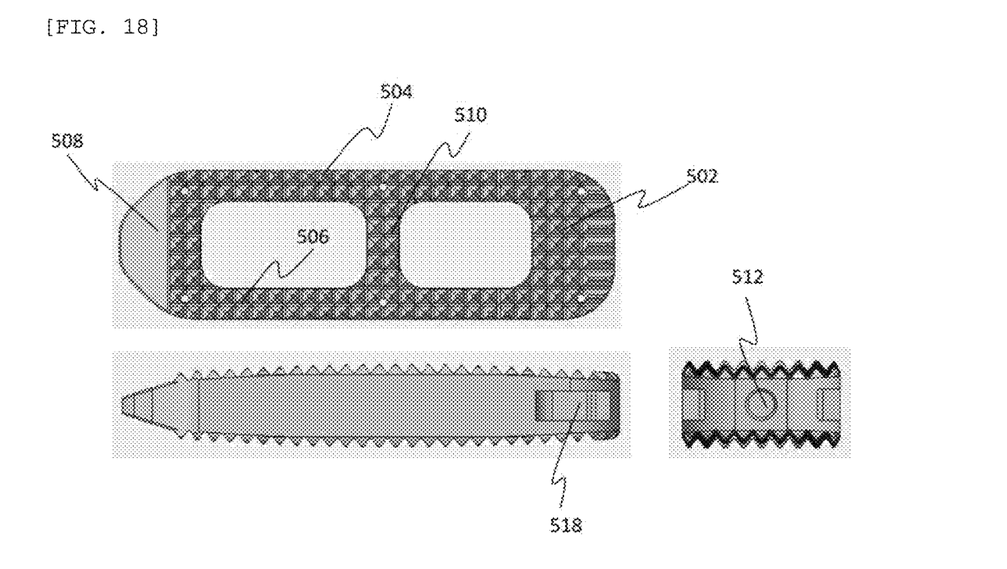
FIG. 18 is a perspective view illustrating a state before mounting a plate in the implant of FIG. 17.
Figure 19:
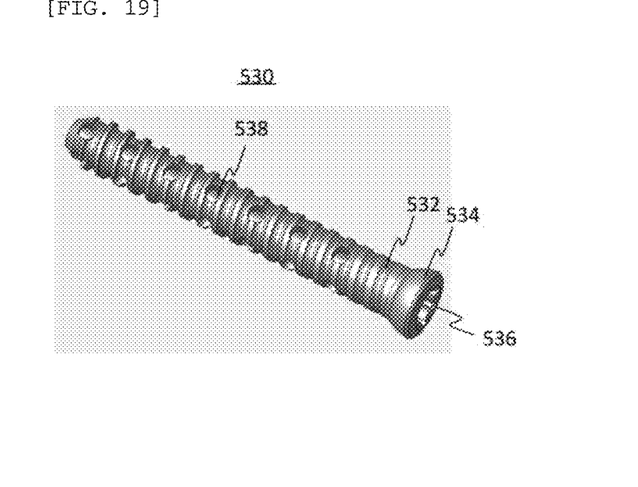
FIG. 19 is a perspective view of a bone screw used in FIG. 17.

Next, an implant 500 of Embodiment 5 will be described with reference to FIGS. 17 to 19.

The implant 500 includes an implant body and an injection unit similar to Embodiment 1. The implant body also includes a proximal part 502, side parts 504 and 506, and a distal part 508, and has holder seats 518 to be coupled with the device for inserting the implant.

The injection unit includes a bone screw 530 mounted on a plate 520 attached to the implant body.

Herein, the implant body is first inserted between the vertebral bodies, and then the plate 520 is fixed to the implant body by screwing a plate fixing screw 526 to a mounting hole 512 formed in the implant body. In this case, the mounting hole 512 may also be utilized as a device mounting hole connected to a device for gripping and inserting the implant body into the vertebral body. The plate 520 includes bone screw receiving holes 522 and 524 formed in at least one of an upper portion and a lower portion thereof. The bone screw 530 is inserted into the vertebral body through the bone screw receiving holes 522 and 524.

The bone screw 530 has an injection port 536 formed in a head 534 thereof and outlet ports 538 formed in a threaded part 532 thereof to be communicated with the injection port 536. The injection port 536 is integrally formed in or connected to a hole, into which a driver (not illustrated) is inserted. In addition, it is preferable that the outlet port 538 has a cross-sectional area decreasing toward the distal part so that the bone material may be constantly flown out.

Figure 20:
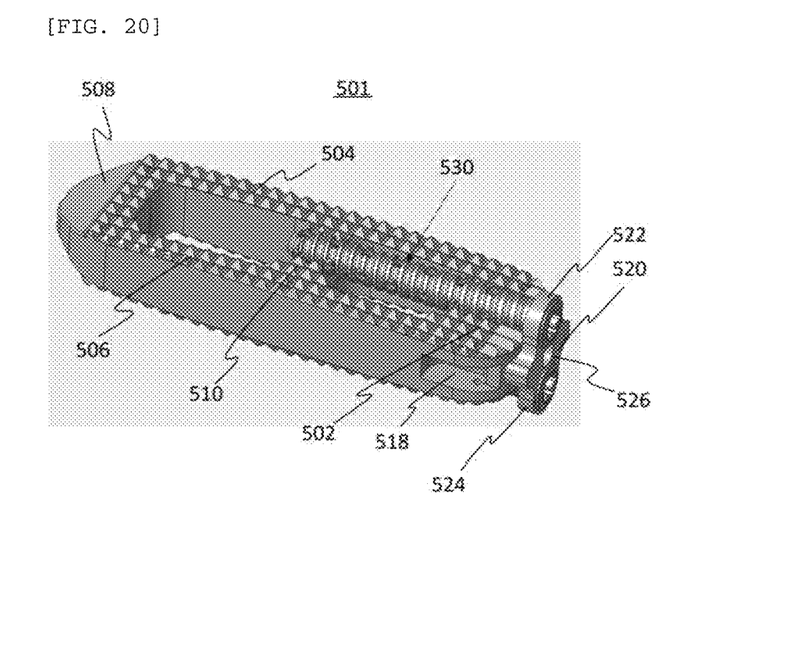
FIG. 20 is a perspective view illustrating an implant according to a variant of Embodiment 5 of the present invention.
Figure 21:
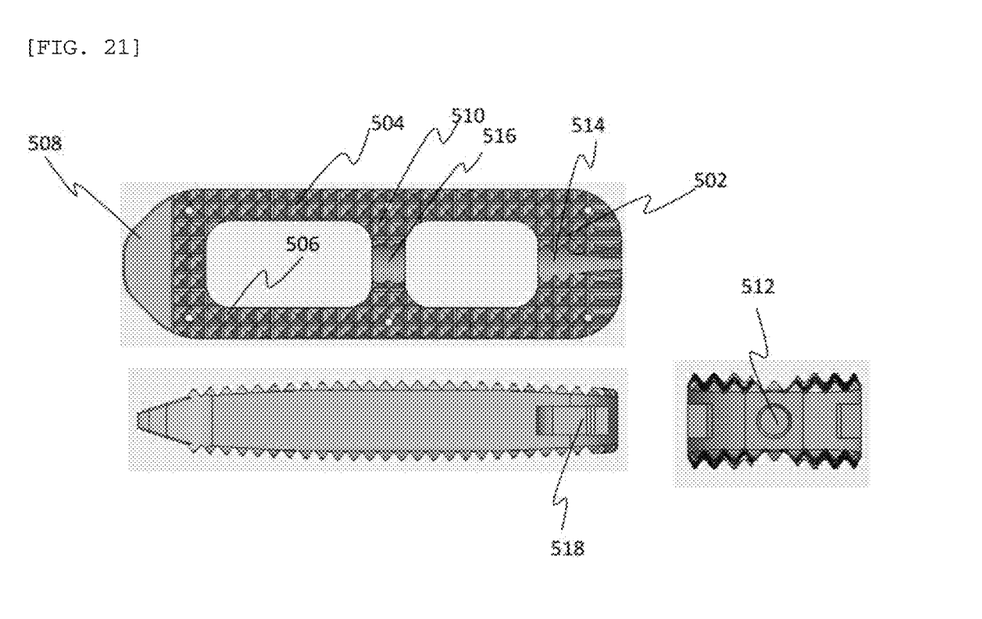
FIG. 21 is a perspective view illustrating a state before mounting a plate in the implant of FIG. 20.

Further, as illustrated in FIGS. 20 and 21, an implant 501 according to a variant of Embodiment 5 may also be considered. The same parts of the implant 501 as the implant 500 of Embodiment 5 will be denoted by the same reference numerals.

The implant 501 may be used when the plate 520 has a small length because an interval between the vertebral bodies is narrow. To this end, the implant 501 may have bone screw seats 514 and 516 formed therein to secure a space, in which the bone screw 530 can be inserted. The bone screw seats 514 and 516 may prevent the implant body from interfering with the bone screw 530 when the bone screw 530 inserted into the vertebral body. In addition, the plate 520 may be fixed to the implant body without using a separate plate fixing screw, or by using a plate fixing screw having a form to cover a portion of the head 534 of the bone screw 530.

While the present invention has been described with reference to the preferred embodiments and variants, the present invention is not limited to the above-described specific embodiments and the variants, and it will be understood by those skilled in the related art that various modifications and variations may be made therein without departing from the scope of the present invention as defined by the appended claims.

The cage according to the present invention does not require a separate implant for fixing the vertebral bodies to each other, and it is possible to expect that the operation time may be reduced to improve the prognosis, and thereby replacing the existing cage.

DESCRIPTION OF REFERENCE NUMERALS 100, 101, 200, 300, 400, 500, 501: Implant
102, 202, 302, 402, 502: Proximal part
104, 106, 204, 206, 304, 306, 404, 406, 504, 506: Side part
108, 208, 308, 408, 508: Distal part
110, 112, 310, 410, 510: Bridge
114: Digger receiving cavity
116: Through hole
118, 218, 318, 418, 518: Holder seat
120, 320, 420: Operation hole
130, 150, 230, 250, 330: Injection unit
132, 152: Digger
134, 154: Injection tube
136, 156, 236, 256, 336, 536: Injection port
138, 158: Injection fastening part
140, 160: Digger blade
142, 162, 238, 258, 340, 538: Outlet port
210, 212: Guide part
220: Guide block
222, 224: Guide port
232, 252: Keel part
234, 254: Slider
240, 260: Tip portion
332: Anchor
334: Stopper
338: Anchor tip
350: Perforation device
352: Perforation device tip
354: Perforation device gripping part
432: Flange
434: Lower part
436: Position retaining protrusion
438: Lower opening
440: Upper part
442: Upper opening
512: Mounting hole
514, 516: Bone screw seat
520: Plate
522, 524: Bone screw receiving hole
526: Plate fixing screw
530: Bone screw
532: Threaded part
534: Head
536: Injection port
538: Outlet port

What is claimed is:

1. An implant assembly comprising:
an implant body inserted between vertebral bodies, the implant body having a top surface, a bottom surface and a longitudinal axis, the top surface having guide parts formed therein; and
an injection unit installed in the implant body, wherein the injection unit is guided by the guide parts, and configured to inject bone cement into the vertebral bodies,
wherein the injection unit further comprises a keel part configured to dig into an end plate in a direction in which the implant body is inserted,
wherein the implant body further comprises a guide block for guiding insertion of the keel part, the guide block comprising guide ports formed therein, the guide ports being vertically arranged along a longitudinal axis of the guide block, so that the keel part is guided through one of the guide ports, and
wherein the longitudinal axis of the guide block extends transverse to the longitudinal axis of the implant body.

2. The implant assembly according to claim 1, wherein the keel part comprises sliders formed on both sides thereof, on which the guide parts move.

3. The implant according to claim 2, wherein the guide block is formed on one side of the implant body.

4. The implant assembly according to claim 1, wherein the keel part comprises a plurality of outlet ports formed therein along a longitudinal direction thereof.

5. The implant assembly according to claim 1, wherein the keel part comprises a sharp tip portion formed at one end thereof to facilitate digging into the vertebral bodies.

6. The implant assembly according to claim 1, wherein a length of the keel part is greater than 50% of a length of the implant body or less than 100% thereof.

* * * * *